United States Patent [19]
Zajaczkowski et al.

[11] Patent Number: 5,576,091
[45] Date of Patent: Nov. 19, 1996

[54] RAISED ELASTICIZED BARRIER FOR ABSORBENT ARTICLE

[75] Inventors: Peter Zajaczkowski, Auburn; Penny Lovestedt, Renton, both of Wash.

[73] Assignee: Paragon Trade Brands, Inc., Federal Way, Wash.

[21] Appl. No.: 291,396

[22] Filed: Aug. 16, 1994

[51] Int. Cl.$^6$ .................................................... B32B 23/02
[52] U.S. Cl. .......................... 428/192; 156/161; 156/164; 156/204; 156/229; 428/284; 428/913; 604/385.2
[58] Field of Search .................................. 428/192, 284, 428/913; 604/385.2; 156/161, 164, 229, 204

[56] References Cited

U.S. PATENT DOCUMENTS

| | | | |
|---|---|---|---|
| 4,662,877 | 5/1987 | Williams | 604/385 |
| 4,764,234 | 8/1988 | Smits et al. | 156/164 |
| 4,795,451 | 1/1989 | Buckley | 604/385 |
| 5,030,303 | 7/1991 | Cucuzza | 156/164 |
| 5,092,861 | 3/1992 | Nomura et al. | 604/385 |
| 5,147,487 | 9/1992 | Nomura et al. | 156/164 |

Primary Examiner—James J. Bell
Attorney, Agent, or Firm—Klarquist Sparkman Campbell Leigh & Whinston, LLP

[57] ABSTRACT

An absorbent article is described which has a moisture-impervious backing layer, a liner sheet comprising an integral sheet, and an absorbent-core layer positioned between the liner sheet and the backing layer. Raised elasticized barrier means form a pocket to receive exudates. The barrier means may include elastic bands that are attached only to the liner sheet in the crotch portion of the article, such as by an adhesive. The liner sheet is bonded to the backing sheet adjacent leg-opening portions of the article, but is not bonded to the backing sheet at regions of the liner sheet adjacent first and second edges of the elastic bands, such as from at least about 5 mm to about 20 mm adjacent the first and second edges of the elastic bands. Preferably, the liner sheet is free of adhesive for a region of about 8 mm to about 12 mm adjacent the first and second edges of the elastic bands. The absorbent article may be substantially hourglass shaped, or substantially rectangular shaped. The elastic bands may be disposed on the inner sheet in a serpentine or linear array. A method for manufacturing the absorbent article also is described.

41 Claims, 5 Drawing Sheets

RAISED ELASTICIZED BARRIER FOR ABSORBENT ARTICLE

FIELD OF THE INVENTION

This invention concerns absorbent articles having a raised elasticized barrier and pocket for containing exudates.

BACKGROUND OF THE INVENTION

Disposable absorbent garments, and the manufacture of such garments, are well known in the art. Disposable absorbent garments typically include a moisture-impervious backing sheet, an absorbent pad, and a body-contacting liner sheet. In addition, such garments also include elasticized regions for securing the garment about the waist and legs of a wearer. These elasticized regions have been produced from varying patterns of the elastic members. Serpentine elasticized areas have been used to form elasticized leg openings. One example of a patent that uses plural spiral elasticized regions to form leg gathers is U.S. Pat. No. 5,092,861.

Despite previous advancements in the field of absorbent garments, persons skilled in the art continue their efforts to produce more comfortable garments which are better able to contain body exudates. For instance, a problem associated with prior art garments has been exudate leakage from the garment. Prolonged contact of exudates with the skin of the wearer also is a problem. Recent absorbent garments have utilized passageways through the liner sheet to help contain such exudates, and to remove them from contact with the wearer. For instance, U.S. Pat. No. 4,990,147 describes an absorbent article having a passageway through the liner sheet which helps isolate waste from the skin of the wearer. Still another example of a garment that includes a passageway through the liner sheet is Khan's U.S Pat. No. 4,968,312.

Although many attempts have been made to provide garments that may be more comfortable and likely function better than previous garments for containing exudates, they also add steps to the manufacturing process. As a result, there still is a need for an economically fashioned absorbent garment which provides a pocket region for containing exudates.

SUMMARY OF THE INVENTION

This invention is directed to an absorbent article that includes a pocket for containing exudates which is formed by providing an elasticized barrier region of the liner sheet. The absorbent article does not require, but may include, an inner layer. Prior art garments that included a pocket typically required an inner layer in addition to a liner sheet. The article of the present invention therefore provides savings in terms of material costs. In general, the article comprises a moisture-impervious backing layer, a liner sheet, and an absorbent core layer that is positioned between the liner sheet and the backing layer. Elasticized inner-layer barrier means also are included to define a pocket for receiving exudates. The barrier means are located substantially in the crotch region of the absorbent article. The elasticized barrier means may comprise an elasticized portion of the liner sheet. Alternatively, the elasticized barrier means may comprise elastic members joined only to the liner sheet in regions adjacent to the absorbent core. The elastic members are not attached to the pad or to the backing sheet in such regions. However, in those regions of the article that define leg openings, the elastic members may have adhesive on both surfaces, so that they attach to both the liner sheet and backing sheet. The formation of the exudate pocket is facilitated by having the elastic members attached only to the liner sheet in regions adjacent the pad and in the crotch of the article. Moreover, the article fits snugly around the legs of a person wearing the article if the elastic members are attached to both the liner sheet and backing sheet in those regions of the article that define leg openings. The liner sheet is not joined to the backing layer or the pad at regions adjacent the elastic members.

The article also may use elastic means to define both leg gathers and a raised elasticized barrier, the barrier defining a pocket region to receive exudates. In regions adjacent the pad in the crotch portion of the article, the elastic means are attached to the liner sheet, such as by an adhesive. The liner sheet is not bonded to the absorbent core and the backing sheet at regions of the liner sheet adjacent to the edges of the elastic means. For instance, the liner sheet is not joined to the absorbent core or backing layer from at least about 5 mm to about 20 mm adjacent the first and second edges of the elastic means, and preferably the liner sheet is not joined to the absorbent core or backing layer for a region of about 8 mm to about 12 mm adjacent the first and second edges of the elastic means.

The absorbent article may be substantially hourglass shaped, or substantially rectangular shaped, with the hourglass shape being a currently preferred embodiment. For embodiments having an hourglass shape, the liner sheet generally has first and second waist edges that are substantially parallel to a transverse axis of the article. The article also includes first and second side edges. The backing layer and the liner sheet define first and second leg openings.

For both hourglass- and rectangular-shaped embodiments, the elastic means may comprise at least a first elongate elastic band that is secured to the liner sheet. A first end portion of the first elongate elastic band is disposed adjacent the first waist edge and extends towards the second waist edge and between the longitudinal axis and the first side edge. The first elastic band has first and second edges, and in the crotch region the liner sheet is free of adhesive adjacent the first and second edges, so that the liner sheet is not bonded to the absorbent core or backing layer in the regions adjacent the elastic bands. The article also includes at least a second elongate elastic band that is secured to the liner sheet, and which has a first end portion disposed adjacent the first waist edge and between the longitudinal axis and the second side edge. The second elastic band has first and second edges as well, and the liner sheet also is free of adhesive adjacent the first and second edges. The region adjacent the first and second edges that is devoid of adhesive, and hence is not bonded to the absorbent core or backing layer, may vary. This distance generally is from about 5 mm to about 20 mm adjacent the first and second edges of the first and second elastic bands, and preferably from about 8 mm to about 12 mm. Both the first elongate elastic band and the second elongate elastic band are attached to both the liner sheet and backing sheet around the leg openings.

For this first embodiment, the article also may include third and fourth elastic bands. The third elastic band is located adjacent the first waist edge and between the first waist edge and the transverse axis. The fourth elastic band is located adjacent the second waist edge and between the second waist edge and the transverse axis. The first-through-fourth elastic bands collectively define a pocket region in the crotch of the article for receiving exudates. The elastic bands collectively gather the liner sheet, separate from the backing sheet, to form the exudate pocket.

Both the hourglass- and rectangular-shaped absorbent articles also may utilize serpentine elastic bands. In the hourglass embodiment, the liner sheet has first and second waist edges that are substantially parallel to a transverse axis of the article, and first and second side edges. The backing layer and the liner sheet define first and second leg openings. The elastic means comprise at least a first elongate elastic band that is secured to the liner sheet in the crotch regions of the article, and secured to both the liner sheet and backing sheet around the leg openings. A first end portion of the first elongate elastic band is disposed adjacent the first leg opening and between the first leg opening and the first waist edge, as well as between the longitudinal axis and the first side edge. The first elastic band extends in a curvilinear path around the first leg opening towards the second waist edge and crosses the longitudinal axis between the second waist edge and the transverse axis. The first elastic band extends in a curvilinear path around the second leg opening and towards the first waist edge. This elastic band then terminates at a second end portion adjacent the second leg opening and between the second leg opening and the first waist edge, as well as between the longitudinal axis and the second edge.

The article also includes at least a second elongate elastic band that is secured only to the liner sheet in the crotch portions of the article, and to the liner sheet and backing sheet around the leg openings. The second elongate elastic band has a first end portion disposed adjacent the first leg opening and between the first leg opening and the second waist edge, as well as between the longitudinal axis and the first side edge. The second elastic band extends in a curvilinear path around the first leg opening towards the first waist edge and crosses the longitudinal axis between the first waist edge and the transverse axis. The second elastic band also extends around the second leg opening and towards the second waist edge. The second elastic band terminates at a second end portion which is adjacent the second leg opening and between the second leg opening and the second waist edge, as well as between the longitudinal axis and the second edge.

This embodiment of the invention also may comprise plural first elongate elastic bands, and plural second elongate elastic bands. In such a case, the plural first elastic bands and the plural second elastic bands define plural first and second elastic band edges. Whether plural elastic bands are used or not, in the crotch region of the article the liner sheet is substantially free of adhesive, and therefore is not bonded to the absorbent core or backing sheet from at least about 5 mm to about 20 mm, preferably from about 8 mm to about 12 mm, adjacent the edges of the elastic means.

If the absorbent garment is rectangular and includes serpentine elastic members, then the first and second waist edges are substantially parallel to a transverse axis of the article, and the first and second side edges also are substantially parallel to the longitudinal axis. The elastic means comprise at least a first elongate elastic band that is secured only to the liner sheet in the crotch region, and to the liner sheet and backing sheet adjacent the leg openings. A first end portion of the first elongate elastic band is disposed adjacent the first waist edge and between the longitudinal axis and the first side edge. The first elastic band extends in a curvilinear path towards the second waist edge and crosses the longitudinal axis between the second waist edge and the transverse axis. The elastic band thereafter extends towards the first waist edge and terminates at a second end portion adjacent the first waist edge and between the longitudinal axis and the second edge. This embodiment also includes at least a second elongate elastic band that is secured only to the liner sheet in the crotch region, and to the liner sheet and backing sheet adjacent the leg openings. The second elongate elastic band has a first end portion that is disposed adjacent the second waist edge and between the longitudinal axis and the first side edge. The second elastic band extends in a curvilinear path towards the first waist edge and crosses the longitudinal axis between the first waist edge and the transverse axis. The second elastic band thereafter extends towards the second waist edge and terminates at a second end portion that is adjacent the second waist edge and between the longitudinal axis and the second edge. The elastic bands collectively define a pocket in the crotch region of the diaper for receiving exudates by gathering the liner sheet, which is not attached to the core or backing sheet, independently of the backing sheet. The article also may utilize plural first and second elongate elastic members. The liner sheet of the article is substantially free of adhesive from at least about 5 mm to about 20 mm, preferably from about 8 mm to about 12 mm, adjacent the edges of the elastic members in the crotch region.

A preferred embodiment of the invention comprises an absorbent article having first and second waist edges that are substantially parallel to a transverse axis of the article, and first and second side edges. The absorbent article includes a moisture-impervious backing layer, a liner sheet having a first major surface adapted to contact the wearer and a second major opposed surface, and an absorbent-core layer positioned between the liner sheet and the backing layer. The backing layer and the liner sheet define first and second leg openings. The absorbent article utilizes plural first and second elongate elastic members that are adhered to both the liner sheet and backing sheet to define leg gathers. In the crotch region, the plural elastic members are attached only to the liner sheet, and thereby form a containment pocket for containing exudates.

The plural first elastic members have plural first end portions that are disposed adjacent the first leg opening and between the first leg opening and the first waist edge. The plural first elastic members also are disposed between the longitudinal axis and the first side edge. The plural first elastic members extend in a sinusoidal path around the first leg opening towards the second waist edge and cross the longitudinal axis between the second waist edge and the transverse axis. The plural first elastic members also extend in a sinusoidal path along the second side edge, towards the first waist edge and around the second leg opening. The plural first elastic bands terminate at plural second end portions that are adjacent the second leg opening and between the second leg opening and the first waist edge, as well as between a longitudinal axis of the article and the second side edge.

The plural second elongate elastic members are secured to only the liner sheet in the crotch region and have plural first end portions that are disposed adjacent the first leg opening and between the first leg opening and the second waist edge. The plural second elastic members are disposed between the longitudinal axis of the article and the first side edge. The second elastic members extend in a sinusoidal path around the first leg opening towards the first waist edge and cross the longitudinal axis between the first waist edge and the transverse axis. The plural second elastic members extend in a sinusoidal path along the second side edge and terminate at plural second end portions adjacent the second leg opening and between the second leg opening and the first waist edge, as well as between the longitudinal axis and the second side edge.

The first and second plural elastic members are disposed in substantially mirror-image sinusoidal paths and, in combination with the liner sheet, form a raised elasticized region of the liner sheet which defines a containment pocket in a crotch region of the article for receiving body exudates. The backing sheet and liner sheet are joined to each other at discrete locations by an adhesive to maintain the core therebetween. The plural first and second elastic members define plural first and second elastic member edges, the backing sheet and liner sheet being free of adhesive in the crotch region for about 5 mm to about 20 mm adjacent the plural first and second elastic member edges, preferably from about 8 mm to about 12 mm. This invention also provides a method for producing an absorbent garment. The method comprises providing at least a first elongate elastic member and at least a second elongate elastic member, an absorbent pad, a sheet of moisture-impervious backing-layer material, and a sheet of liner sheet material. The sheets of backing and liner sheet material each have opposed first and second waist edge regions and first and second side edges on opposite sides of the longitudinal axis of the sheet. The backing layer and the liner sheet also may define first and second leg openings. At least a singular first elastic member has a first end portion disposed adjacent the first leg opening and between the first leg opening and the first waist edge, as well as between the longitudinal axis and the first side edge. The first elastic member extends around the first leg opening in a curvilinear path towards the second waist edge and crosses the longitudinal axis between the second waist edge and the transverse axis. The first elastic member extends along the second side edge and around the second leg opening and terminates at a second end portion adjacent the second leg opening and between the second leg opening and the first waist edge, as well as between the longitudinal axis and the second edge.

At least a singular second elastic member has a first end portion disposed adjacent the first leg opening and between the first leg opening and the second waist edge, as well as between the longitudinal axis and the first side edge. The second elastic member extends in a curvilinear path around the first leg opening towards the first waist edge and crosses the longitudinal axis between the first waist edge and the transverse axis. The second elastic member extends around the second leg opening and along the second side edge and terminates at a second end portion adjacent the second leg opening and between the second leg opening and the second waist edge, as well as between the longitudinal axis and the second edge.

The liner sheet and the backing sheet are placed in coincident facing relationship with the pad therebetween. The liner sheet and backing sheets are joined together at discrete locations with an adhesive with the pad therebetween. However, in the crotch region the backing sheet and liner sheet are substantially free of adhesive adjacent the edges of the first and second elastic members.

Accordingly, a first object of this invention is to provide an absorbent article that includes an improved containment pocket.

Another object is to provide an improved containment pocket which eliminates the additional manufacturing steps required to form a cut-out pocket region in the liner sheet.

Another object of this invention is to provide an absorbent article which forms a raised elasticized barrier for containing exudates.

Another object of one embodiment of this invention is to attach plural elastic members to a liner sheet in the crotch region with the liner sheet being substantially devoid of adhesive in regions adjacent edge portions of the plural elastic members, thereby allowing for the formation of a containment pocket and a raised elasticized barrier for containing exudates.

An advantage of the present invention is that it eliminates the need to form a cut-out pocket region for containing exudates.

DETAILED DESCRIPTION OF THE PREFERRED EMBODIMENTS

I. Absorbent Articles

Figure 1:
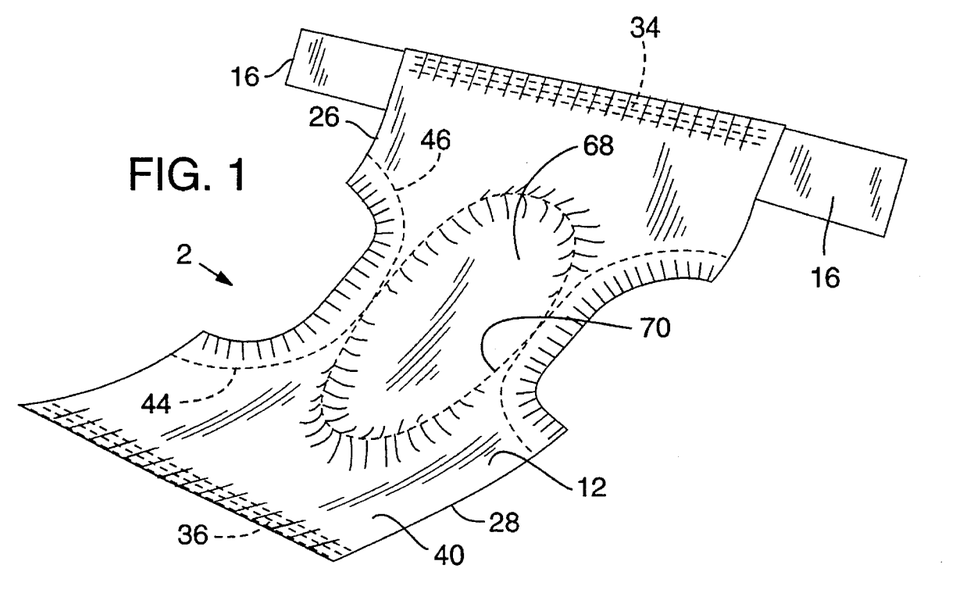
FIG. 1 is a perspective view illustrating an absorbent garment according to the present invention having a raised elasticized barrier.
Figure 2:
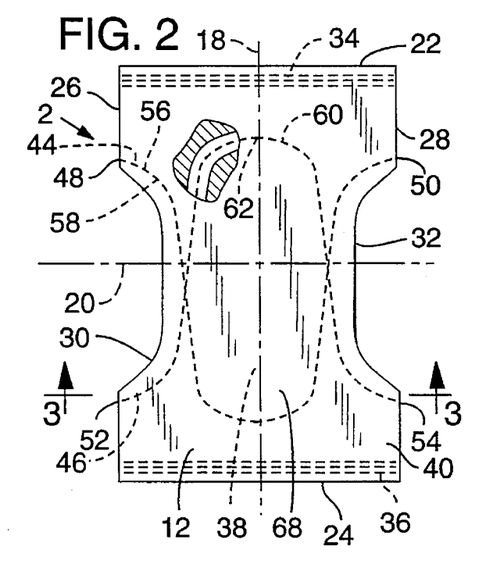
FIG. 2 is a plan view of an hourglass-shaped absorbent article according to the present invention having serpentine elastic members.
Figure 3:
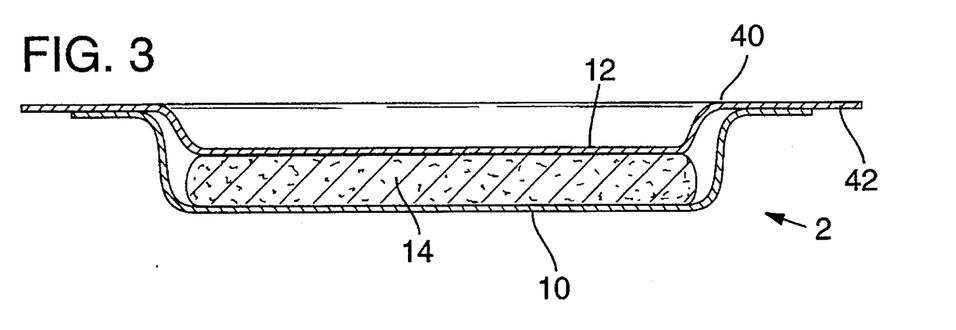
FIG. 3 is a cross-sectional view of the absorbent article of FIG. 2 taken along line 3—3.
Figure 5:
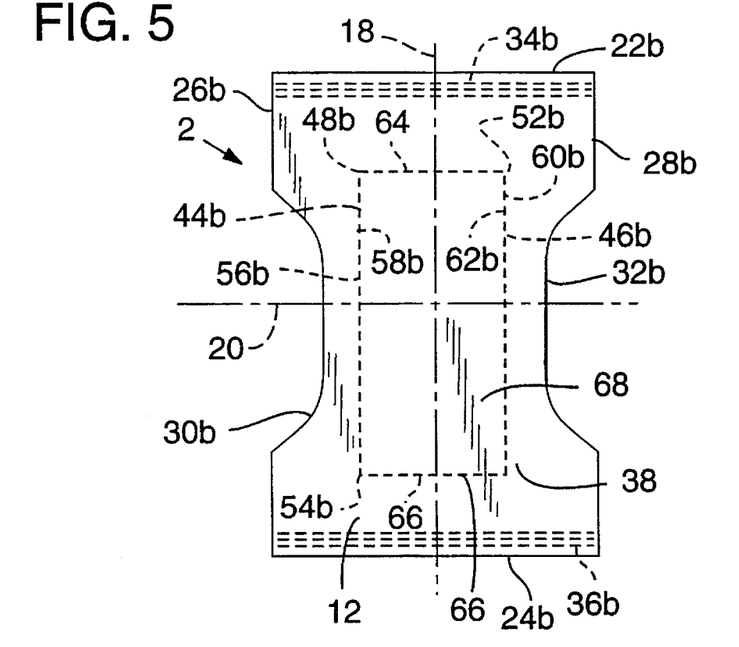
FIG. 5 is a plan view of an hourglass-shaped absorbent article according to the present invention illustrating an alternative placement of the elastic members.
Figure 6:
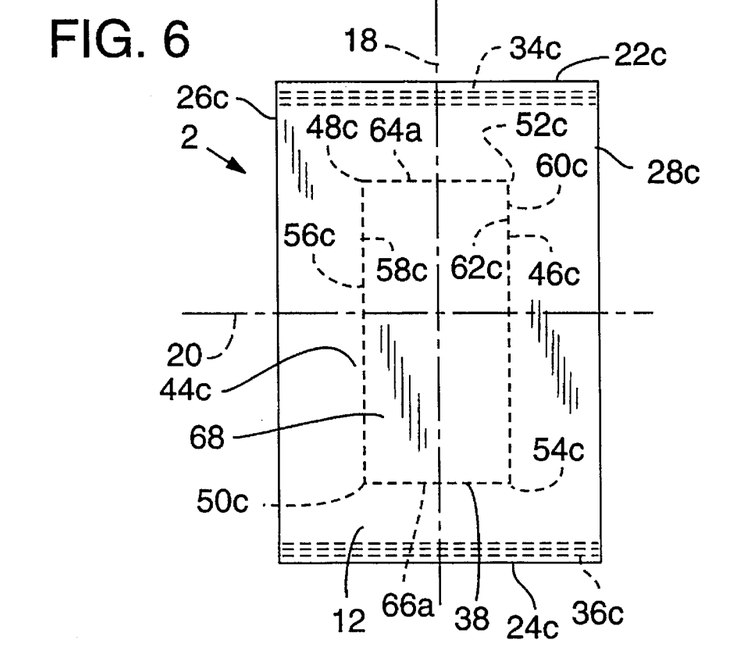
FIG. 6 is a plan view of a rectangular-shaped absorbent article according to the present invention illustrating an alternative placement of the elastic members.
Figure 7:
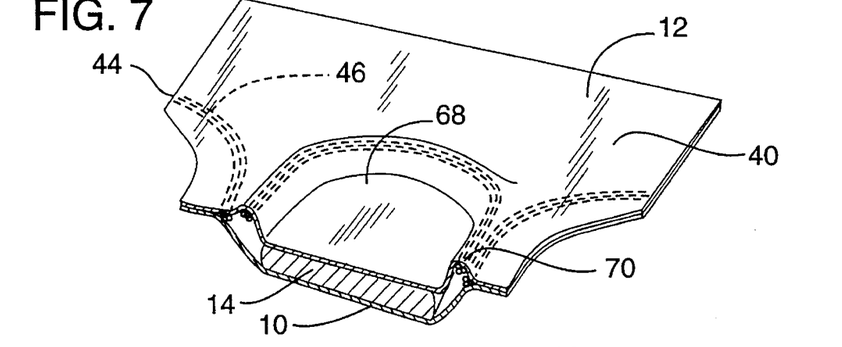
FIG. 7 is a fragmentary perspective view of the absorbent article of FIG. 1.

FIGS. 1–7 illustrate various disposable absorbent articles 2 manufactured in accordance with the present invention. Absorbent article 2 includes a moisture-impervious backing layer 10 (FIGS. 3 and 7), liner sheet 12, and a moisture-absorbent layer, core or pad 14 (FIGS. 3 and 7). The pad 14 is supported on backing layer 10, and is disposed between the backing layer 10 and the liner sheet 12, as shown by FIG. 3. FIGS. 1–7 illustrate article 2 having only backing layer 10 and liner sheet 12. However, one skilled in the art will appreciate that additional layers, such as an additional impervious layer, also can be added to form article 2 according to the present invention.

As discussed in more detail below, the liner sheet 12 and backing layer 10 may be bonded together, at least in the leg-opening portion of the article, by any known means. One example of a method for bonding the layers 10 and 12 together is to place an adhesive in discrete locations. A second example of a method for securing the layers 10 and 12 together is to sonically bond the individual layers together.

Absorbent core or pad 14 typically is made of a wood pulp or other absorbent fibers, such as a commercially available fluff pulp or a fluffed soft-wood pulp. Core or pad 14 may have a substantially hourglass-shape. Alternatively, the pad 14 also may have a substantially rectangular shape. The absorbent core or pad 14 is generally located in a crotch region 38 of the article 2. Superabsorbent particulate matter can be used in combination with the wood pulp or absorbent fibers to produce a core 14 having included therein superabsorbent particulate materials.

FIG. 1 illustrates an absorbent article 2 according to the present invention. Garment 2 typically is used as a baby or infant diaper, or as an adult incontinence brief. As shown in FIGS. 1 and 2, the absorbent article 2 may include stretchable waistband regions 34 and 36. Also, article 2 can include tapes or other fasteners 16 located at the waist region for securing article 2 about the waist of a person wearing the article. FIG. 1 shows a pair of tape fasteners 16 as one illustrated embodiment of fasteners useful for securing the article 2 to the body of a wearer. Tape fasteners 16 are indicated as extending generally outwardly to opposite sides of the garment, and adjacent one of the ends of article 2.

The manufacture of disposable absorbent garments, baby or infant diapers and adult incontinence briefs as illustrated in the figures generally is known in the art. For instance, absorbent articles and methods for their manufacture are illustrated in U.S. Pat. Nos. 4,726,807 and 4,687,477. Each of these U.S. patents is hereby incorporated by reference.

The moisture impervious backing layer 10 typically is made from a thin thermoplastic material such as a polyethylene film having a thickness in the range of about 0.02 mm to about 0.04 mm. The thermoplastic material may be a pigmented material as well. The liner sheet 12 typically is an integral sheet of a moisture pervious material. Liner sheet 12 may comprise a composite material having different degrees of moisture permeability. A particularly suitable material for forming liner sheet 12 is a spun-bond polypropylene material having a basis weight of about 0.6 ounces per square yard. However, one skilled in the art of absorbent garment manufacture will realize that there is a wide variety of materials that may be used to form backing layer 10, liner sheet 12, and the absorbent core 14. This invention is intended to encompass all such materials, and is not limited to the specific materials that are discussed herein as exemplary materials.

As shown in FIGS. 2, and 4–6, absorbent article 2 has a longitudinal axis 18 and a transverse axis 20. The absorbent article 2 typically has a first laterally extending waist edge 22 and a second laterally extending waist edge 24, which is spaced longitudinally from the first waist edge 22. The waist edges 22 and 24 typically are substantially parallel to the transverse axis 20. The first and second waist edges 22 and 24 lie along the ventral and dorsal regions of the wearer during use. The absorbent article 2 also includes first side edges 26 and 28.

FIGS. 2 and 5 illustrate a substantially hourglass-shaped article 2. The illustrated embodiment includes a first in-cut leg opening 30 and a second in-cut leg opening 32. These in-cut leg portions 30 and 32 gather about the legs of a wearer during use. As worn, the illustrated embodiments in FIGS. 2 and 5 adapt to a substantially hourglass-shaped configuration wherein tape fasteners 16 extend outwardly from opposite side margins, typically from the dorsal waist portion and extend to the ventral waist portion of the garment for fastening thereto. Waist gathers 34 and 36 also can be used with the article 2 of the present invention. Such waist gathers 34 and 36 may be provided adjacent the first waist edge 22 and second waist edge 24, respectively. Waist gathers 34 and 36 extend transversely of the garment and provide a more secure and comfortable fit for the wearer.

II. Elastic Members

The present invention is directed to a new and improved absorbent article 2. The combination of elastic means substantially located in the crotch region, and the selection of the placement of securing means, such as an adhesive, to secure the elastic members to the liner sheet, and to the backing layer in the leg opening regions 30 and 32, provide for a raised, elasticized barrier region which contains bodily exudates. As used herein, "elastic means" refers to any structural component that may be used to form elasticized regions of the absorbent article 2, such as natural rubber, polyurethane, lycra strands, or other materials used in the industry. Moreover, the elastic means function with the liner sheet 12 to form a raised elasticized barrier that defines a containment pocket 68 for receiving exudates.

With specific reference to the liner sheet 12, which preferably is composed of a nonwoven moisture pervious material, it should be understood that liner sheet 12 has a first major surface 40 which is adapted to contact the wearer, and a second major opposed surface 42. The moisture pervious material used to form the liner sheet 12 directs exudates toward a containment pocket 68 that is defined in the crotch region of the article 2 as discussed in more detail below.

As illustrated in FIG. 2, the article 2 includes at least a first elongate elastic member, or band, 44 and a second elongate elastic member, or band, 46. First elastic member 44 has a first end portion 48 and a second end, or terminus, portion 50. Similarly, the second elastic member 46 has a first end portion 52 and a second end, or terminus, portion 54. It should be understood by one skilled in the art that the absorbent article 2 also may include plural elastic members, such as plural first elastic members 44 and plural second elastic members 46. In crotch region 38, the elastic members 44 and 46 are secured to opposed major surface 42 of liner sheet 12 using any suitable means, such as an adhesive. In the leg opening regions 30 and 32, the elastic members are secured to both the liner sheet 12 and backing sheet 10.

FIG. 2 illustrates one particular embodiment of a useful curvilinear, or sinusoidal, pattern for placing elastic members 44 and 46 relative to the liner sheet 12. The illustrated embodiment in FIG. 2 shows that the first elastic member 44 has a first end portion 48 that is disposed adjacent the first leg opening 30 and between the first leg opening 30 and the first waist edge 22. The first elastic member 44 extends in a substantially curvilinear, or sinusoidal, path around the first leg opening 30 and towards the second waist edge 24. The first elastic member 44 crosses the longitudinal axis 18 between the second waist edge 24 and the transverse axis 20. The first elastic member 44 thereafter extends in a substantially curvilinear path around the second leg opening 32 and towards the first waist edge 22 to terminate at a second end portion 50 which is adjacent the second leg opening 32 and between the second leg opening 32 and the first waist edge 22. The terminus portion 50 also is located between the longitudinal axis 18 and the second side edge 28. First elastic member 44 also has a first edge 56 and a second edge 58.

FIG. 2 also illustrates that the second elastic member 46 is disposed in the substantially mirror-image curvilinear, or sinusoidal, curve pattern compared to the first elastic member 44. More particularly, the second elastic member 46 has a first end portion 52 that is disposed adjacent the first leg opening 30 and between the first leg opening 30 and the second waist edge 24. The second elastic member 46 also is located between the longitudinal axis and the first side edge 26. Second elastic member 46 extends in a substantially curvilinear path around the first leg opening 30 and towards the first waist edge 22. The second elastic member crosses the longitudinal axis 18 between the first waist edge 22 and the transverse axis 20. The second elastic member 46 extends in a curvilinear path around the second leg opening 32 and towards the second waist edge 24 to terminate at a second end portion 54 adjacent the second leg opening 32 and between the second leg opening 32 and the second waist edge 24. The second end portion also terminates at a position between the longitudinal axis 18 and the second side edge 28. The second elastic 46 has a first edge 60 and a second edge 62.

Thus, as illustrated in FIG. 2, the elastic members 44 and 46 define substantially mirror-image serpentine paths and are secured only to the liner sheet 12 in the crotch region 38. The inverse sinusoidal curves defined by the curvilinear paths of the elastic bands 44 and 46 cooperatively define a pocket 68 that is located in the crotch region 38 of the article 2. Again, as stated above, it will be understood that although the invention has been described with singular first and second elastic bands 44 and 46, the invention also may comprise plural first elastic members 44 and plural second elastic members, or bands, 46.

Figure 4:
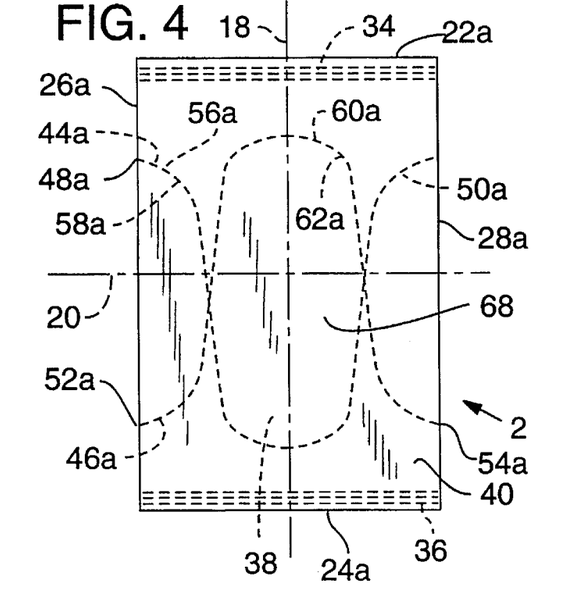
FIG. 4 is a plan view of a rectangular-shaped absorbent article according to the present invention having serpentine elastic members.

FIG. 4 illustrates a second embodiment of the present invention having a substantially rectangular shape. In the illustrated embodiment, first elastic member 44a has a first end portion 48a. The elastic member 44a is secured only to the liner sheet 12 in the crotch region 38. The first end portion 48a of the first elastic member 44a is disposed adjacent the first waist edge 22a. The first elastic member 44a extends in a substantially curvilinear, or sinusoidal, path towards the second waist edge 24a and between the longitudinal axis 18 and the first side edge 26a. The first elastic band 44a has a first elastic band edge 56a and a second elastic band edge 58a. The first elastic band 44a has a first end portion 48a that is disposed adjacent the first waist edge 22a. The first end portion 48a also is disposed between the longitudinal axis 18 and the first side edge 26a. The first elastic band 44a extends in a substantially curvilinear path toward the second waist edge 24a and crosses the longitudinal axis 18 between the second waist edge 24a and the transverse axis 20. The first elastic band 44a then extends in a substantially curvilinear path towards the first waist edge 22a to terminate at a second end portion 50a which is adjacent the first waist edge 22a as well as between the longitudinal axis 18 and the second side edge 28a.

Second elastic band 46a is disposed in a substantially mirror image sinusoidal or curvilinear path as the first band member 44a. More specifically, a second elastic member 46a, which is attached only to liner sheet 12 in crotch region 38, has a first end portion 52a that is disposed adjacent the second waist edge 24a as well as between the longitudinal axis 18 and the first side edge 26a. The second elastic band 46a extends in a substantially curvilinear path towards the first waist edge 22a and crosses the longitudinal axis 18 between the first waist edge 22a and the transverse axis 20. The second elastic band 46a thereafter extends toward the second waist edge 24a and terminates at a second end portion 54a. Terminus portion 54a is disposed adjacent the second waist edge 24a, as well as between the longitudinal axis 18 and the second side edge 28a.

FIG. 5 illustrates still a third embodiment of the present invention and the placement of the elastic band members 44b and 46b. The embodiment of article 2 illustrated in FIG. 5 has a substantially hourglass shape. The liner sheet 12 includes a first waist edge 22b and a second waist edge 24b. The article 2 also includes a first leg opening region 30b and a second leg opening region 32b. The article 2 illustrated in FIG. 5 includes a first elongate elastic band 44b that is secured only to the liner sheet 12 in the crotch region 38. A first end portion 48b of the elastic member 44b is disposed adjacent the first waist edge 22b and extends towards the second waist edge 24b between the longitudinal axis 18 and the first side edge 26b. The first elastic band 48b terminates in a first terminus portion 54b. The elastic band 44b also includes a first elastic band edge 56b and a second elastic band edge 58b.

The article 2 also includes a second elongate elastic band 46b that is secured only to the liner sheet 12 in the crotch region and has a first end portion 52b that is disposed adjacent the first waist edge 22b, and also disposed between the longitudinal axis 18 and the second side edge 28b. The second elastic band 46b has first and second edges 60b and 62b. The elastic bands 44b and 46b are substantially parallel relative to the longitudinal axis 18 of article 2.

The embodiment illustrated in FIG. 5 may also include a third elastic band 64 and a fourth elastic band 66. Elastic band 64 is located adjacent the first waist edge 22b and between the first waist edge 22b and the transverse axis 20. The fourth elastic band 66 is located adjacent the second waist edge 24b and between the second waist edge 24b and the transverse axis 20. The elastic bands 64 and 66 are positioned substantially parallel to the transverse axis 20 and are secured only to the liner sheet in the crotch region. The elastic bands 44b, 46b, 64 and 66 collectively deform the liner sheet to define a pocket region 68 in crotch region 38 of article 2.

Still another embodiment of the article 2 is illustrated in FIG. 6. The embodiment illustrated in FIG. 6 has a substantially rectangular shape. Article 2 includes a first waist edge 22c and a second waist edge 24c, as well as a first side edge 26c and a second side edge 28c. Article 2 also includes at least a first elongate elastic band 44c, which is secured only to the liner sheet 12 in crotch region 38. Band 44c has a first end portion 48c that is disposed adjacent the first waist edge 22c and extends toward the second waist edge 24c between the longitudinal axis 18 and a first side edge 26c. The first band member 44c terminates in terminus portion 50c adjacent the waist edge 24c.

The article 2 illustrated in FIG. 6 also includes at least a second elastic member 46c also is attached only to the liner sheet 12 in the crotch region 38. Elastic band 46c has a first end portion 52c that is disposed adjacent to the first waist edge 22c. Band member 46c extends from the first waist edge 22c towards the second waist edge 24c, and terminates adjacent waist edge 24c with terminus end portion 54c. The first elastic band 44c has a first band edge 56c and a second band edge 58c. Second elastic member 46c has a first elastic band edge 60c and a second edge 62c.

The embodiment of article 2 illustrated in FIG. 6 also may include a third elastic band 64a and a fourth elastic band 66a also attached only to the liner sheet in the crotch region. Elastic band 64a is located adjacent the first waist edge 22c and between the first waist edge 22c and the transverse axis 20. The fourth elastic band 66a is located adjacent the second waist edge 24c and between the second waist edge 24c and the transverse axis 20. The first-through-fourth elastic bands 44c, 46c, 64a and 66a, collectively deform the liner sheet to define a pocket region 68 in the crotch region 38 of article 2.

Figure 10:
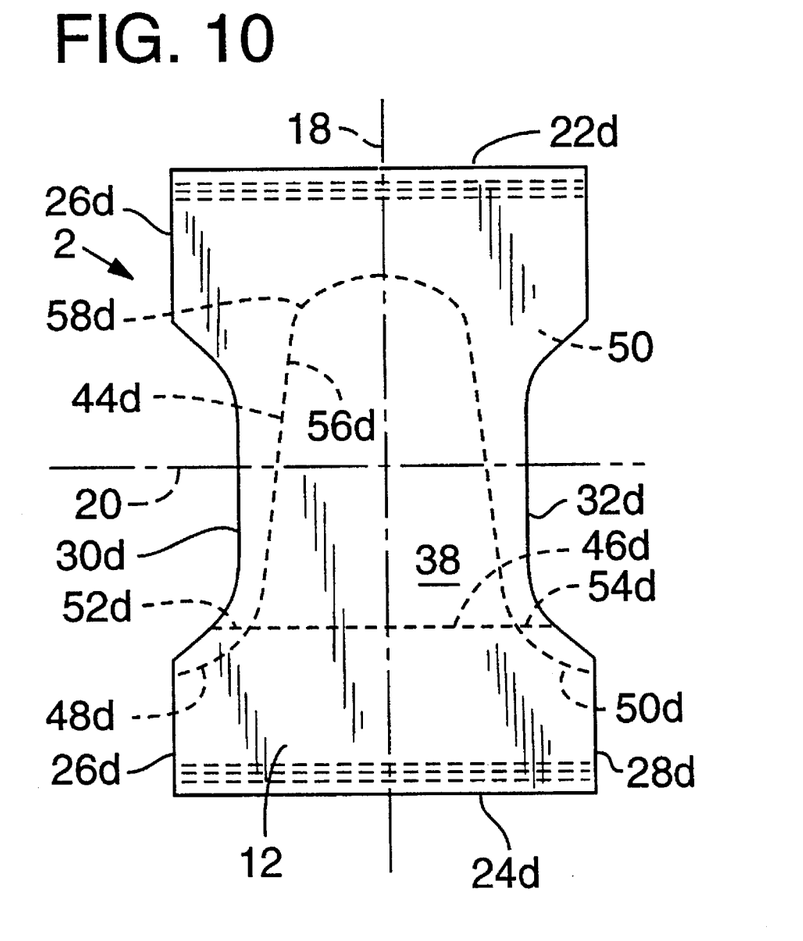
FIG. 10 is a plan view of an hourglass-shaped absorbent article according to the present invention illustrating an alternative placement of elastic members.

A further embodiment of article 2 is illustrated in FIG. 10. The illustrated embodiment has a substantially hourglass-shape as previously discussed in relation to FIGS. 2 and 5 and its general construction is similar to those described in relation to FIGS. 2 and 5.

However, in the embodiment illustrated in FIG. 10 the elastic members designated here as 44d, 46d are dispersed in a different relationship than in prior embodiments. The liner sheet 12 includes a first waist edge 22d and a second waist edge 24d. The article 2 also includes a first leg opening region 30d and a second leg opening region 32d. The elastic members, or bands, 44d and 46d are secured only to the liner sheet 12 in the crotch region 38. A first end portion 48d of elastic member 44d is disposed adjacent side edge 26d between transverse axis 20 and waist edge 24d. The elastic member 44d extends in a curvilinear path around a portion of leg opening 30d and toward the other waist edge 22d between the longitudinal axis 18 and side edge 26d. Elastic member 44d then extends across axis 18 and in a curvilinear path around a portion of leg opening 32d and terminates in a terminus portion 50d adjacent side edge 28d and between transverse axis 20 and waist edge 24d. The elastic band 44d also includes opposed first and second elastic band edges 56d, 58d.

The article also includes a second elongate elastic band 46d secured only to the liner sheet 12 in crotch region 38. As seen in FIG. 10, elastic band 46d extends transversely of the article substantially parallel to axis 20, between axis 20 and waist edge 24d. The elastic band 46d has first and second end portions 52d, 54d, respectively, which are adjacent leg openings 30d, 32d respectively. Band 46d intersects band 44d adjacent leg openings 30d, 32d.

III. Elasticized Barrier Region and Containment Pocket

The preceding paragraphs describe the positioning of elastic means, such as elastic bands 44 and 46. Elastic bands 44 and 46 are secured to the liner sheet 12 by means known in the art, such as an adhesive. Liner sheet 12 is not attached to absorbent core 14 and backing sheet 10 in the region of the elastic bands in crotch region 38. An important aspect of the present invention is both the location and pattern of the elastic members, such as 44 and 46, as well as the bonding of the liner sheet 12 to the backing layer 10. Prior-art absorbent garments have formed pockets for receiving body exudates by removing a portion, such as an oval portion, from the liner sheet 12. This adds processing steps to the manufacture of the article 2, and also adds to the expense associated therewith. The present invention forms a pocket 68 for receiving body exudates, but does not require that the liner sheet 12 be processed to define a cut-out region.

The pocket 68 may be formed by raised elasticized barrier means. As used herein, "raised elasticized barrier means" refers to a liner sheet structure 12 that is free to separate from the absorbent core 14 and backing layer 10 in selected portions of crotch region 38. This can be accomplished, for instance, by providing a heat-activated elastic portion of the liner sheet 12. In such an article the liner sheet 12 may be elasticized by applying heat to sheet 12, such as by using heated rollers. Alternatively, the elasticized barrier means may be formed by securing elastic means, such as members 44 and 46, to the liner sheet 12.

As a result, elastic members 44 and 46, along with having certain regions of the liner sheet 12 not joined to backing layer 10 and the absorbent core 14, collectively form the raised elasticized barrier region 70. The raised elasticized barrier region 70 is illustrated in FIGS. 1 and 7. Because the elastic members 44 and 46 are attached to the liner sheet 12, and because the liner sheet 12 is not bonded to absorbent core 14 or backing layer 10 at certain discrete regions, the liner sheet 12 is retracted separately from the backing layer 10 and absorbent core 14, thereby allowing for the subsequent formation of the pocket 68 and the raised region 70. The pocket area 68, which lies interiorly of band members 44 and 46, sags upon receiving body exudates. This allows the liner sheet 12 to provide a pocket 68 and a raised elasticized barrier region 70, which protects the user of the article 2 from exudate leaks and contact with the exudate.

As shown in FIGS. 1–2 and 4–6, the elastic bands 44 and 46 include first opposed elastic band edges 56 and 58 and second opposed elastic band edges 60 and 62, respectively. The elastic members 44, 46, 64 and 66 are bonded directly to the liner sheet 12 in the crotch portion 38 at regions directly beneath the elastic members 44, 46, 64 and 66. However, at areas immediately adjacent to edges 56, 58, 60 and 62 and within crotch area 68, the liner sheet 12 is not bonded to the backing layer 10 or to core 14. This region of nonbonding extends for approximately 5 mm to about 20 mm adjacent each edge of the elastic members 44 and 46, and preferably extends from about 8 mm to about 12 mm. The combination of the placement of the elastic members 44 and 46, along with leaving certain regions of liner sheet 12 not bonded to backing layer 10, allows for the raising or retraction of the liner sheet 12, and the subsequent formation of the elasticized barrier region 70.

Elastic members 44, 46 typically are bonded to liner sheet 12 in a stretched or tensioned condition. As used herein, the term "bonded" refers to adhesive bonding, sonic bonding, heat bonding, solid bonding, stitching or any other method of affixing the elastic members 44, 46 to the liner sheet 12. The elastic members may comprise any elastic member suitable for use with article 2, such as a natural rubber elastic that can be obtained from Fulflex, Inc., of Middletown, R.I. This material typically is stretched lengthwise prior to being affixed to liner sheet 12. However, other elastic materials also may be used, such as a heat-activated material, for example, a thermally activated elastic TAE from 3M Company. Other elastic materials which may be used to practice the present invention include natural rubber, polyurethane, ribbon elastic, lycra strands, or others used in the industry.

IV. Method and Apparatus

Figure 8:
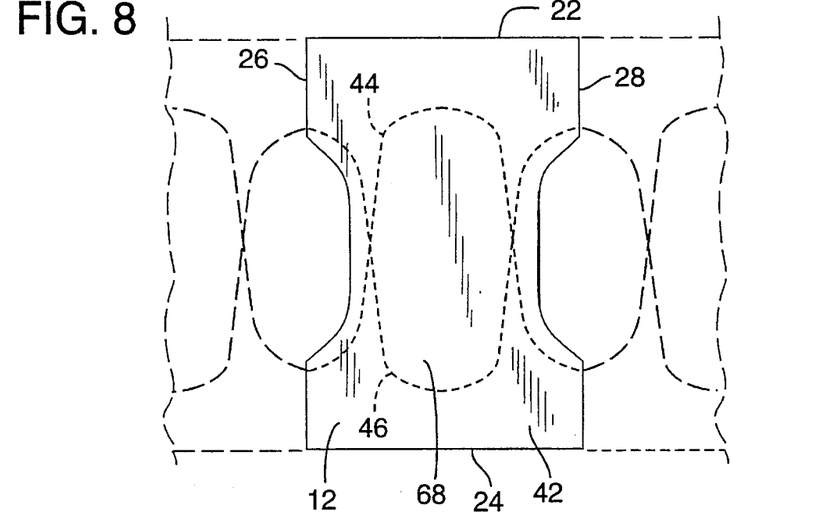
FIG. 8 is a plan view illustrating the positional relationship of an liner sheet material and elastic members during a process for manufacturing absorbent articles according to the present invention.
Figure 9:
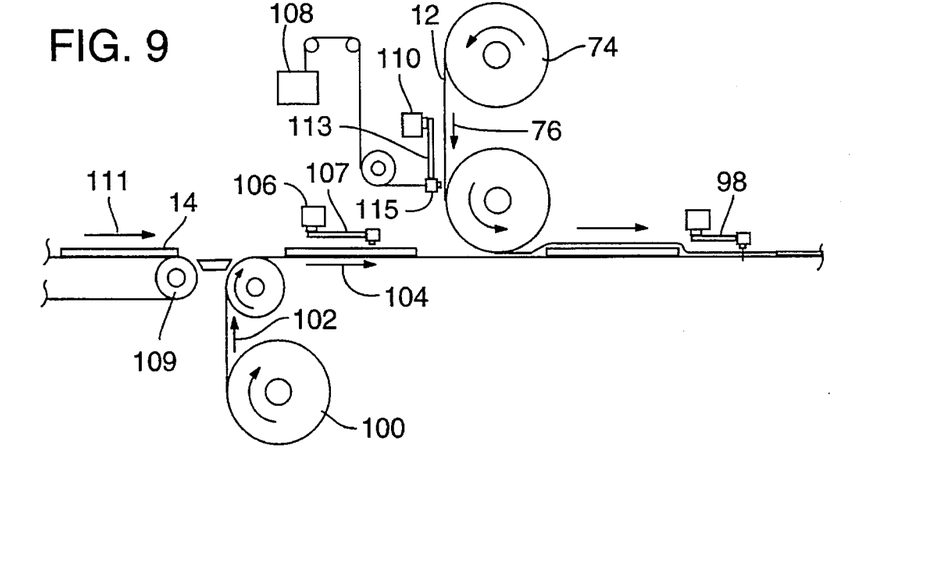
FIG. 9 is a schematic side elevation view of an apparatus which may be used in performing manufacturing methods according to the present invention.

A method and apparatus for producing an absorbent article 2 according to the invention are shown schematically in FIGS. 8 and 9. Initially, the backing layer 10 and pad 14 are assembled. An elongate web of backing layer 10 is drawn from a roll 100 (FIG. 9) in the direction of arrows 102 and 104. A spray device 106, having a swing-arm 107, places adhesive on selected portions of sheet web 100. Pad 14 is then positioned on top of backing material 10 by conveyor 109 moving in the direction of arrow 111.

Concurrently with the assembly of the backing sheet 10 and pad 14, the liner sheet 12 is being produced. Initially, an elongate web of liner sheet material 12 is drawn from a roll 74 and carried in the direction of arrow 76. The bottom surface 42 of liner sheet 12 is sprayed with a pattern of adhesive as shown generally in dashed line in FIG. 8 by applicators such as 112 having a swing-arm 113. The adhesive pattern is substantially continuous along sheet 12 and has a width preferably no greater than the width of the pattern of the elastic members 44 and 46 to be applied thereto. Elastic members 44 and 46 are drawn from a reservoir indicated generally at 108 and are applied to liner sheet 12 through elastic applicators, such as applicator 115, which may be attached to oscillating arm 113. As a result, oscillating arms 113 can be used to apply both adhesive and elastic members 44, 46 in the same preselected pattern. Elastic members 44, 46 are applied to sheet 12 in a tensioned form. Elastic members 44, 46 may be placed on sheet 12 in overlapping sinusoidal curves, as illustrated in FIGS. 2 and 4, or may be placed in a substantially parallel relationship to the longitudinal transverse axis, as shown in FIGS. 5 and 6.

The combined liner sheet 12, elastic members 44, 46, core 14, and backing sheet 10, are then adhered or joined to each other using, for example, an adhesive, sonic bonding or heat bonding. Any such bonding or adhering pattern used to join the component parts of the assembly must leave a region surrounding the elastic members in the crotch region free of the underlying backing sheet and core to permit the forming of the exudate-receiving pocket. However, the central crotch region of the liner sheet may be adhered to core 14 in regions spaced from the elastic members.

Thereafter, swing-arm waterjet cutters, such as that indicated generally at 98 in FIG. 9, may cut out the article 2, as well as any leg openings 30 and 32 that may be used, as illustrated in FIGS. 2 and 5. A final transverse knife, or cutter, (not shown) is operable to sever individual garments from the continuous flow product produced in the method just described.

The present invention has been described with reference to several preferred embodiments. Other embodiments of the invention will be apparent to those skilled in the art from a consideration of this specification or practice of the invention disclosed herein. It is intended that the specification and examples contained herein be considered as exemplary only, with the true scope and spirit of the invention being indicated by the following claims.

We claim:

1. An absorbent article, comprising:
   a moisture-impervious backing layer;
   a liner sheet comprising an integral sheet;
   an absorbent core layer positioned between the liner sheet and the backing layer;
   elastic means for forming a raised elasticized barrier which defines a pocket for receiving exudates, the elastic means being attached only to the liner sheet in a crotch region of the absorbent article, wherein the liner sheet is not joined to the backing sheet or the absorbent core at regions extending to opposite sides of the elastic means to permit raising of the liner sheet from the backing layer to form the pocket.

2. The article according to claim 1 wherein the elastic means is attached to the liner sheet using an adhesive, and wherein the liner sheet is free of adhesive at regions adjacent first and second edges of the elastic means.

3. The article according to claim 2 wherein the liner sheet is free of adhesive and is not bonded to the backing layer from at least about 5 mm to about 20 mm adjacent the first and second edges of the elastic means.

4. The article according to claim 3 wherein the liner sheet is free of adhesive for a region of about 8 mm to about 12 mm adjacent the first and second edges of the elastic means.

5. The article according to claim 1 wherein the article has a substantially hourglass shape.

6. The article according to claim 5 wherein the liner sheet has first and second waist edges substantially parallel to a transverse axis of the article, and first and second side edges, the backing layer and the liner sheet defining first and second leg openings, and wherein the elastic means comprise:
   a first elongate elastic band that is secured to the liner sheet, a first end portion of the first elongate elastic band being disposed adjacent the first waist edge and extending towards the second waist edge and between the longitudinal axis and the first side edge, the first elastic band having first and second edges, the liner sheet being free of adhesive adjacent the first and second edges; and
   a second elongate elastic band that is secured to the liner sheet and having a first end portion disposed adjacent the second waist edge and extending towards the first waist edge between the longitudinal axis and the second side edge, the second elastic band having first and second edges, the liner sheet being free of adhesive adjacent the first and second edges.

7. The article according to claim 6 wherein the liner sheet is free of adhesive from about 5 mm to about 20 mm adjacent the first and second edges of the first and second elastic bands.

8. The article according to claim 6 and including a third band and fourth elastic band, the third elastic band being located adjacent the first waist edge and between the first waist edge and the transverse axis, the fourth elastic band being located adjacent the second waist edge and between the second waist edge and the transverse axis, the first through fourth elastic bands collectively defining a pocket region in the crotch of the article for receiving exudates.

9. The article according to claim 5 wherein the liner sheet has first and second waist edges that are substantially parallel to a transverse axis of the article, and first and second side edges, the backing layer and the liner sheet defining first and second leg openings, and wherein the elastic means comprise:
   a first elongate elastic band secured to the liner sheet, a first end portion of the first elongate elastic band being disposed adjacent the first leg opening and between the first leg opening and the first waist edge, as well as between the longitudinal axis and the first side edge, the first elastic band extending in a curvilinear path around the first leg opening towards the second waist edge and crossing the longitudinal axis between the second waist edge and the transverse axis, the first elastic band extending in a curvilinear path around the second leg opening and towards the first waist edge and terminating at a second end portion adjacent the second leg opening and between the second leg opening and the first waist edge, as well as between the longitudinal axis and the second edge; and
   a second elongate elastic band secured to the liner sheet and having a first end portion disposed adjacent the first leg opening and between the first leg opening and the second waist edge, as well as between the longitudinal axis and the first side edge, the second elastic band extending in a curvilinear path around the first leg opening towards the first waist edge and crossing the longitudinal axis between the first waist edge and the transverse axis, the second elastic band extending around the second leg opening and towards the second waist edge and terminating at a second end portion adjacent the second leg opening and between the second leg opening and the second waist edge, as well as between the longitudinal axis and the second edge.

10. The absorbent article according to claim 9 comprising plural first elongate elastic bands, and plural second elongate elastic bands.

11. The absorbent article according to claim 10 wherein the plural first elastic bands and the plural second elastic bands define plural first and second elastic band edges, the liner sheet of the article being substantially free of adhesive from at least about 5 mm to abut 20 mm adjacent the plural first and second edges of the elastic means.

12. The article according to claim 11 wherein the liner sheet of the article is substantially free of adhesive for about 8 mm to about 12 mm adjacent the plural first and second edges of the elastic means.

13. The article according to claim 1 wherein the article has a substantially rectangular shape.

14. The article according to claim 13 wherein the liner sheet has first and second waist edges substantially parallel to a transverse axis of the article, and first and second side edges substantially parallel to the longitudinal axis, and wherein the elastic means comprise:
  a first elongate elastic band secured to the liner sheet, a first end portion of the first elongate elastic band being disposed adjacent the first waist edge and extending towards and terminating adjacent the second waist edge and between the longitudinal axis and the first side edge, the first elastic band having first and second edges, the liner sheet being free of adhesive adjacent the first and second edges; and
  a second elongate elastic band secured to the liner sheet, a first end portion of the second elastic band being disposed adjacent the first waist edge and extending towards and terminating adjacent the second waist edge and between the longitudinal axis and the second side edge, the second elastic band having first and second edges, the liner sheet being free of adhesive adjacent the first and second edges.

15. The article according to claim 14 wherein the liner sheet is free of adhesive from about 5 mm to about 20 mm adjacent the first and second edges of the first and second elastic bands.

16. The article according to claim 15 and including a third band and a fourth elastic band, the third elastic band being located adjacent the first waist edge and between the first waist edge and the transverse axis, the fourth elastic band being located adjacent the second waist edge and between the second waist edge and the transverse axis, the first through fourth elastic bands collectively defining a pocket region in the crotch of the article for receiving exudates.

17. The article according to claim 13 wherein the article has first and second waist edges that are substantially parallel to a transverse axis of the article, and first and second side edges that are substantially parallel to the longitudinal axis, and wherein the elastic means comprise:
  a first elongate elastic band secured to the liner sheet, a first end portion of the first elongate elastic band being disposed adjacent the first waist edge and between the longitudinal axis and the first side edge, the first elastic band extending in a curvilinear path towards the second waist edge and crossing the longitudinal axis between the second waist edge and the transverse axis, the first elastic band thereafter extending towards the first waist edge and terminating at a second end portion adjacent the first waist edge and between the longitudinal axis and the second edge; and
  a second elongate elastic band secured to the liner sheet and having a first end portion disposed adjacent the second waist edge and between the longitudinal axis and the first side edge, the second elastic band extending in a curvilinear path towards the first waist edge and crossing the longitudinal axis between the first waist edge and the transverse axis, the second elastic band thereafter extending towards the second waist edge and terminating at a second end portion adjacent the second waist edge and between the longitudinal axis and the second edge.

18. The article according to claim 17 wherein the elastic bands collectively define a pocket region located in a crotch region of the diaper for receiving exudates.

19. An absorbent article having first and second waist edges parallel to a transverse axis of the article, and first and second side edges, comprising:
  a moisture-impervious backing layer;
  a liner sheet having a first major surface adapted to contact the wearer, and a second major opposed surface;
  an absorbent core layer positioned between the liner sheet and the backing layer, the liner sheet and the backing layer being secured to each other at discrete locations of contact adjacent leg-opening portions of the article;
  a first elongate elastic member which is secured only to the liner sheet in a crotch portion of the article and which has a first end portion that is disposed adjacent the first waist edge and between the longitudinal axis and the first side edge, the first elastic member extending towards the second waist edge and terminating at a second end portion adjacent the second waist edge and between the longitudinal axis and the first side edge;
  a second elongate elastic member which is secured only to the liner sheet in a crotch portion and having a first end portion disposed adjacent the first waist edge and between the longitudinal axis and the second side edge, the elastic member extending from the first waist edge towards the second waist edge, the second elastic member terminating at a second end portion adjacent the second waist edge and between the longitudinal axis and the second side edge; and
  wherein the first and second elastic members have first and second edges, the liner sheet being free of adhesive in the crotch portion from about 5 mm to about 20 mm adjacent the first and second edges of the elastic members.

20. The article according to claim 19 and further comprising plural first and second elongate elastic members.

21. The article according to claim 20 which further comprises third and fourth elongate elastic members, the third elastic member being positioned adjacent the first waist edge and being substantially parallel to the transverse axis of the article, the third elastic member having a first end portion adjacent the first side edge and extending towards and terminating adjacent the second side edge, and the fourth elastic member being positioned adjacent the second waist edge and being substantially parallel to the transverse axis of the article, the fourth elastic member having a first end portion adjacent the first side edge and extending towards and terminating adjacent the second side edge, the first through fourth elastic members defining a pocket located in a crotch region of the article for containing exudates.

22. An absorbent article having first and second waist edges substantially parallel to a transverse axis of the article, and first and second side edges, comprising:
  a moisture-impervious backing layer;
  a liner sheet having a first major surface adapted to contact the wearer and a second major opposed surface;

an absorbent core layer positioned between the liner sheet and the backing layer, the liner sheet and backing layer defining first and second leg openings;

at least a first elongate elastic member that is secured only to the liner sheet in a crotch portion of the article and which has a first end portion that is disposed adjacent the first leg opening and between the first leg opening and the first waist edge, the first elastic member also being disposed between the longitudinal axis and the first side edge, the first elastic member extending in a curvilinear path around the first leg opening towards the second waist edge and crossing the longitudinal axis between the second waist edge and the transverse axis, the first elastic member also extending in a curvilinear path along the second side edge and around the second leg opening to terminate at a second end portion adjacent the second leg opening and between the second leg opening and the first waist edge, as well as between a longitudinal axis of the article and the second edge;

at least a second elongate elastic member that is secured only to the liner sheet in the crotch portion and which has a first end portion that is disposed adjacent the first leg opening and between the first leg opening and the second waist edge, the second elastic member also being disposed between the longitudinal axis of the article and the first side edge, the second elastic member extending in a curvilinear path around the first leg opening towards the first waist edge and crossing the longitudinal axis between the first waist edge and the transverse axis, the second elastic member also extending in a curvilinear path along the second side edge and terminating at a second end portion adjacent the second leg opening and between the second leg opening and the first waist edge, as well as between the longitudinal axis and the second edge; and wherein the backing sheet and liner sheet are joined to each other at discrete locations adjacent the first and second leg opening by an adhesive, thereby maintaining the core therebetween, the first and second members defining first and second elastic member edges, the backing sheet and liner sheet being free of adhesive adjacent the first and second elastic member edges in the crotch region.

23. The absorbent article according to claim 22 wherein the elastic bands and the liner sheet form a raised elasticized barrier that define a pocket for receiving exudates.

24. The article according to claim 22 and further comprising plural first elastic members and plural second elastic members.

25. The garment according to claim 22 wherein the first and second elastic members are disposed in substantially mirror-image curvilinear paths.

26. The garment according to claim 25 wherein the curvilinear path for the elastic members defines a substantially sinusoidal curve.

27. The article of claim 22 wherein each of the first and second elastic members have a first edge and a second edge, and wherein the backing sheet and liner sheet are free of adhesive for about 5 mm to about 20 mm adjacent the first and second edges of the elastic members.

28. The article according to claim 27 wherein the elastic members and the liner sheet form an elasticized raised portion of the absorbent article.

29. The article according to claim 22 wherein the elastic members have a first edge and a second edge, and wherein the backing sheet and liner sheet are free of adhesive for about 8 mm to about 12 mm adjacent the first and second edges of each of the first and second elastic members.

30. An absorbent article having first and second waist edges that are substantially parallel to a transverse axis of the article, and first and second side edges, comprising:

a moisture-impervious backing layer;

a liner sheet having a first major surface adapted to contact the wearer and a second major opposed surface;

an absorbent core layer positioned between the liner sheet and the backing layer, the backing layer and the liner sheet defining first and second leg openings;

plural first elongate elastic members that are secured only to the liner sheet in a crotch portion of the article and which have plural first end portions that are disposed adjacent the first leg opening and between the first leg opening and the first waist edge, the plural first elastic members also being disposed between the longitudinal axis and the first side edge, the plural first elastic members extending in a curvilinear path around the first leg opening towards the second waist edge and crossing the longitudinal axis between the second waist edge and the transverse axis, the plural first elastic members also extending in a curvilinear path along the second side edge and around the second leg opening to terminate at plural second end portions adjacent the second leg opening and between the second leg opening and the first waist edge, as well as between a longitudinal axis of the article and the second edge;

plural second elongate elastic members that are secured only to the liner sheet in the crotch region and which have plural first end portions that are disposed adjacent the first leg opening and between the first leg opening and the second waist edge, the plural second elastic members being disposed between the longitudinal axis of the article and the first side edge, the second elastic members extending in a curvilinear path around the first leg opening towards the first waist edge and crossing the longitudinal axis between the first waist edge and the transverse axis, the plural second elastic members further extending along the second side edge and terminating at plural second end portions adjacent the second leg opening and between the second leg opening and the first waist edge, as well as between the longitudinal axis and the second side edge, the first and second plural elastic members being disposed in substantially mirror-image curvilinear paths; and wherein the backing sheet and liner sheet are joined to each other at discrete locations adjacent the first and second leg openings by an adhesive, thereby maintaining the core therebetween, the plural first and second elastic members defining plural first and second elastic member edges, the backing sheet and liner sheet being free of adhesive for about 5 mm to about 20 mm adjacent the plural first and second elastic member edges.

31. The article according to claim 30 wherein the curvilinear paths for the plural first and second elastic members define substantially sinusoidal curves.

32. The article according to claim 30 wherein the plural first and second elastic members define a raised elasticized region and in combination define a pocket in a crotch region of the article for receiving exudates.

33. An absorbent article having first and second waist edges that are substantially parallel to a transverse axis of the article, and first and second side edges, comprising:

a moisture-impervious backing layer;

a liner sheet having a first major surface adapted to contact the wearer and a second major opposed surface;

an absorbent core layer positioned between the liner sheet and the backing layer, the backing layer and the liner sheet defining first and second leg openings;

plural first elongate elastic members that are secured to the liner sheet and which have plural first end portions that are disposed adjacent the first leg opening and between the first leg opening and the first waist edge, the plural first elastic members also being disposed between the longitudinal axis and the first side edge, the plural first elastic members extending in a sinusoidal path around the first leg opening towards the second waist edge and crossing the longitudinal axis between the second waist edge and the transverse axis, the plural first elastic members also extending in a curvilinear path along the second side edge towards the first waist edge and around the second leg opening to terminate at plural second end portions adjacent the second leg opening and between the second leg opening and the first waist edge, as well as between a longitudinal axis of the article and the second side edge;

plural second elongate elastic members that are secured to the liner sheet and which have plural first end portions that are disposed adjacent the first leg opening and between the first leg opening and the second waist edge, the plural second elastic members being disposed between the longitudinal axis of the article and the first side edge, the second elastic members extending in a sinusoidal path around the first leg opening towards the first waist edge and crossing the longitudinal axis between the first waist edge and the transverse axis, the plural second elastic members extending in a sinusoidal path along the second side edge and terminating at plural second end portions adjacent the second leg opening and between the second leg opening and the first waist edge, as well as between the longitudinal axis and the second side edge, the first and second plural elastic members being disposed in substantially mirror-image curvilinear paths and in combination forming a raised elasticized region of the liner sheet which defines a pocket in a crotch region of the article for receiving body exudates; and wherein the backing sheet and liner sheet are joined to each other at discrete locations by an adhesive to maintain the core therebetween, the plural first and second elastic members defining plural first and second elastic member edges, the backing sheet and liner sheet being free of adhesive for about 5 mm to about 20 mm adjacent the plural first and second elastic member edges.

34. A method for producing an absorbent garment having a longitudinal and a transverse axis, comprising the steps of:

providing first and second elongate elastic members, an absorbent pad, a sheet of moisture impervious backing layer material, and a sheet of liner sheet material, the sheets of backing and liner sheet material each having opposed first and second waist edge regions and first and second side edges on opposite sides of the longitudinal axis of the sheet, the backing layer and the liner sheet defining first and second leg openings;

securing a first elastic member to the liner sheet material so that the first elastic member has a first end portion disposed adjacent the first leg opening and between the first leg opening and the second waist edge, as well as between the longitudinal axis and the first side edge, the first elastic member extending around the first leg opening in a curvilinear path towards the second waist edge and crossing the longitudinal axis between the second waist edge and the transverse axis, the first elastic member extending along the second side edge and around the second leg opening in a curvilinear path and terminating at a second end portion adjacent the second leg opening and between the second leg opening and the first waist edge as well as between the longitudinal axis and the second edge;

securing at least a second elastic member to the liner sheet so that the second elastic member has a first end portion disposed adjacent the first leg opening and between the first leg opening and the second waist edge, as well as between the longitudinal axis and the first side edge, the second elastic member extending in a curvilinear path around the first leg opening towards the first waist edge and crossing the longitudinal axis between the first waist edge and the transverse axis, the second elastic member extending around the second leg opening and along the second side edge and terminating at a second end portion adjacent the second leg opening and between the second leg opening and the first waist edge, as well as between the longitudinal axis and the second edge;

placing the liner sheet and the backing sheet in coincident facing relationship with the pad therebetween; and joining the liner sheet and backing sheets together with the pad therebetween, the backing sheet and liner sheet not being joined together at regions of from about 5 mm to about 20 mm adjacent first and second edges of the first and second elastic members.

35. The method according to claim 34 and including the steps of providing plural first elastic members and plural second elastic members.

36. An absorbent article, comprising:

a moisture-impervious backing layer;

a liner sheet joined to the backing layer;

an absorbent core layer positioned between the liner sheet and the backing layer; and elasticized inner-layer barrier means which define a pocket for receiving exudates, the barrier means being located substantially in a crotch region of the absorbent article.

37. The article according to claim 36 wherein the elasticized barrier means comprise an elasticized portion of the liner sheet.

38. The article according to claim 36 wherein the elasticized barrier means comprises elastic members joined to the liner sheet, the liner sheet not being joined to the backing layer at regions adjacent the elastic members.

39. An absorbent article, comprising:

a moisture impervious backing layer;

a liner sheet having first and second waist edges substantially parallel to a transverse axis of the article and first and second side edges, with the backing layer and liner sheet defining first and second leg openings;

an absorbent core layer positioned between the liner sheet and backing layer; and elastic means for forming a raised elasticized barrier which defines a pocket for receiving exudates, the elastic means being attached only to the liner sheet in a crotch region of the absorbent article, wherein the liner sheet is not joined to the backing sheet or the absorbent core at regions extending to opposite sides of the elastic means to permit raising of the liner sheet from the backing layer to form a pocket, the elastic means comprising:

a first elongate elastic band secured to the liner sheet and having a first end portion disposed adjacent the first leg opening and between the transverse axis and one waist edge, the first elastic band extending in a curvilinear path around at least a portion of the first leg opening toward the other waist edge and crossing the longitudinal axis between the other waist edge and the transverse axis, the first elastic band extending in a curvilinear path around a portion of the second leg opening and toward the one waist edge and terminating at a second end portion adjacent the second leg opening and between the transverse axis and the one waist edge; and a second elongate elastic band secured to the liner sheet and having a first end portion disposed adjacent the first leg opening between the transverse axis and the one waist edge, and extending transversely of the longitudinal axis to a second end portion disposed adjacent the second leg opening between the transverse axis and the one waist edge.

40. The article of claim 39, wherein the portion of the second elongate elastic band intermediate its first and second portion extends substantially parallel to the transverse axis.

41. The article of claim 40, wherein said second elastic band intersects said first elastic band in a first region adjacent said first leg opening and in a second region adjacent said second leg opening.

* * * * *